United States Patent [19]
Terasawa et al.

[11] Patent Number: 5,957,840
[45] Date of Patent: Sep. 28, 1999

[54] PINCH DEVICE FOR DETECTING A BIOMEDICAL SIGNAL

[75] Inventors: Harutoshi Terasawa; Hitoshi Niwa, both of Tokyo, Japan

[73] Assignee: Nihon Kohden Corporation, Tokyo, Japan

[21] Appl. No.: 08/943,114

[22] Filed: Oct. 3, 1997

[30]     Foreign Application Priority Data

Oct. 3, 1996  [JP]  Japan .................................. 8-262952

[51] Int. Cl.$^6$ ....................................................... A61B 5/00
[52] U.S. Cl. .............................. 600/310; 600/344; 24/504
[58] Field of Search ................................. 600/309, 310, 600/322, 323, 324, 340, 344; 24/504, 543; 606/151, 157

[56]                References Cited

U.S. PATENT DOCUMENTS

| | | |
|---|---|---|
| 3,810,460 | 5/1974 | Van Nie .................................. 600/479 |
| 4,685,464 | 8/1987 | Goldberger et al. . | |
| 5,313,940 | 5/1994 | Fuse et al. . | |
| 5,551,423 | 9/1996 | Sugiura . | |
| 5,666,952 | 9/1997 | Fuse et al. .............................. 600/310 |

FOREIGN PATENT DOCUMENTS 668720  9/1994  Japan .

*Primary Examiner*—Eric F. Winakur
*Attorney, Agent, or Firm*—Sughrue, Mion, Zinn, Macpeak & Seas, PLLC

[57]                ABSTRACT

A pinch device for detecting a biomedical signal which pinches a measuring site of a living body in order to detect a biomedical signal, includes a pair of body members which are opposed to each other, said body members being rotatably coupled to each other via a shaft portion, a movable member mounted to a tip end of one of said paired body members so as to be rotatable, and said movable member having a contact face opposed to another contact face which is formed at a tip end of another one of said paired body members, and a spring member urging said contact face of said movable member and said other contact face of said body member which is opposed to said movable member, in an approaching direction.

4 Claims, 2 Drawing Sheets

PINCH DEVICE FOR DETECTING A BIOMEDICAL SIGNAL

BACKGROUND OF THE INVENTION

1. Field of the Invention

The invention relates to a pinch device for detecting a biomedical signal which pinches a finger, a nose, or an ear of a living body in order to detect a biomedical signal such as a pulse wave.

2. Related Art

FIG. 4 shows the configuration of an example of a prior art pinch device of this kind. Referring to FIG. 4, a pair of body members 1 and 2 are rotatably coupled to each other at their middle portions through a rotation shaft 3. The body members 1 and 2 are configured so as to be substantially symmetrical to each other with respect to the rotation shaft 3. The tip ends of the body members 1 and 2 are inwardly projected. Contact faces 1a and 2a are disposed at the projection ends so as to be opposed to each other, respectively. Driving portions 1b and 2b are disposed integrally with the rear ends of the body members 1 and 2 which are opposite to the tip ends with respect to the rotation shaft 3, respectively.

A substantially U-like spring member 4 is disposed on the outer peripheries of the body members 1 and 2 with placing the middle portion of the spring member at the rotation shaft 3. The ends of the spring member 4 are engaged with halfway positions between the tip ends of the body members 1 and 2 and the rotation shaft 3, respectively. These positions function as the points of application of the spring member 4. An LED 5 serving as a light emitting member, and a PD 6 serving as a light receiving member are embedded in the tip ends of the body members 1 and 2, respectively, and covered by a transparent resin so as to be flush with the contact faces 1a and 2a, respectively.

When a biomedical signal is to be detected by using the thus configured pinch device, the driving portions 1b and 2b are first inwardly pressed by fingers so that the contact faces 1a and 2a of the body members 1 and 2 are separated from each other. Next, a measuring site of a living body, for example, an ear 7 is inserted between the contact faces 1a and 2a and the driving portions are then released, so that the ear 7 is elastically pinched with the urging force exerted by the spring member 4. The LED 5 is then powered on and the PD 6 receives light transmitted through the ear 7 to detect a biomedical signal such as a pulse wave. Lead wires connected to the LED 5 and the PD 6 are not shown.

In the pinch device of the prior art configured as described, particularly when a measuring site of a living body is thick, the contact faces 1a and 2a of the body members 1 and 2 make point contact or line contact with the measuring site of the living body, so that the measuring site cannot be pinched by a uniform pressure. As a result, there arises a problem in that the pinch device is unstably attached and data of the detected biomedical signal are incorrect.

SUMMARY OF THE INVENTION

The invention has been conducted in view of these circumstances. It is an object of the invention to provide a pinch device for detecting a biomedical signal which can pinch a measuring site of a living body with a uniform pressure so that a biomedical signal can be correctly detected.

In order to attain the object, in the invention, a pinch device for detecting a biomedical signal which pinches a measuring site of a living body in order to detect a biomedical signal comprises a pair of body members which are opposed to each other, middle portions of the body members being rotatably coupled to each other via a shaft portion; a movable member which is mounted to a tip end of one of the paired body members via a spherical rotation shaft so as to be rotatable in any direction, and which has a contact face opposed to another contact face which is formed at a tip end of another one of the paired body members; and a spring member which urges the contact face of the movable member and the other contact face of the body member which is opposed to the movable member, in an approaching direction.

According to the configuration, the movable member on which one of the contact faces is formed is mounted to one of the body members via the spherical rotation shaft so as to be rotatable in any direction. In the case where a measuring site is to be pinched between the paired body members, even when the surface of the measuring site is tilted in any direction, therefore, the contact face can closely abut against the surface. As a result, the pinch device can pinch the measuring site in all the contact faces with a uniform pressure, so that a biomedical signal can be correctly detected.

DETAILED DESCRIPTION OF THE PREFERRED EMBODIMENTS

Hereinafter, an embodiment of the pinch device for detecting a biomedical signal of the invention will be described with reference to the accompanying drawings.

Figure 1:
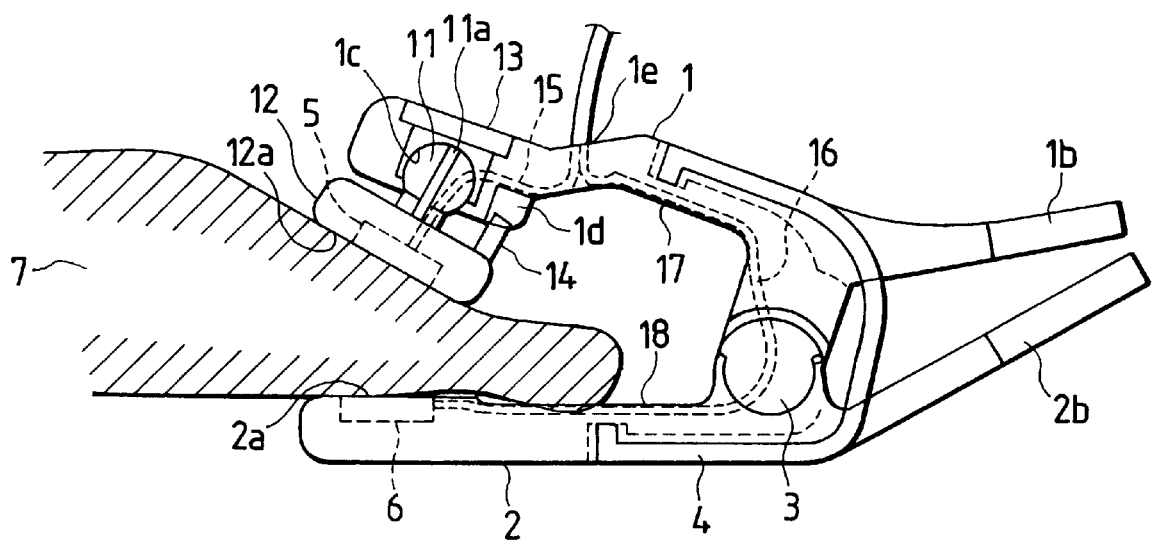
FIG. 1 is a side view showing the configuration of an embodiment of the pinch device for detecting a biomedical signal of the invention.
Figure 2:
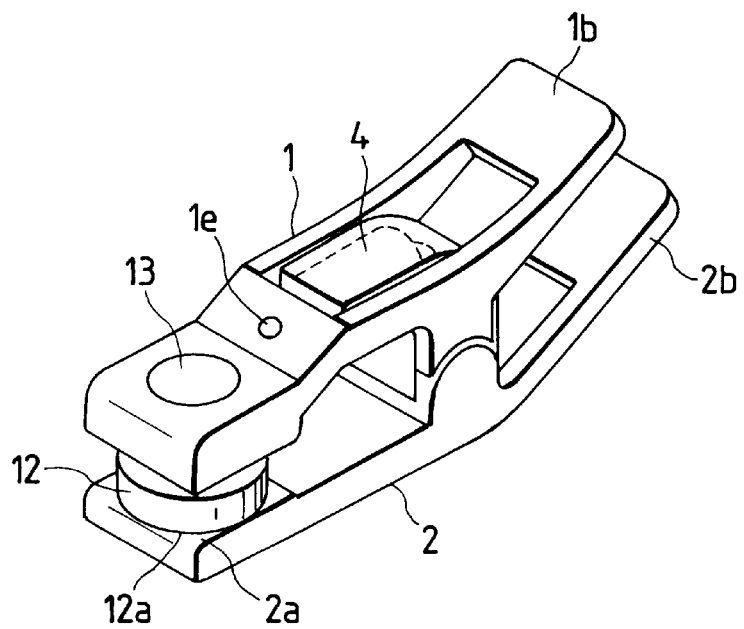
FIG. 2 is a perspective view showing the whole appearance of FIG. 1.
Figure 3:
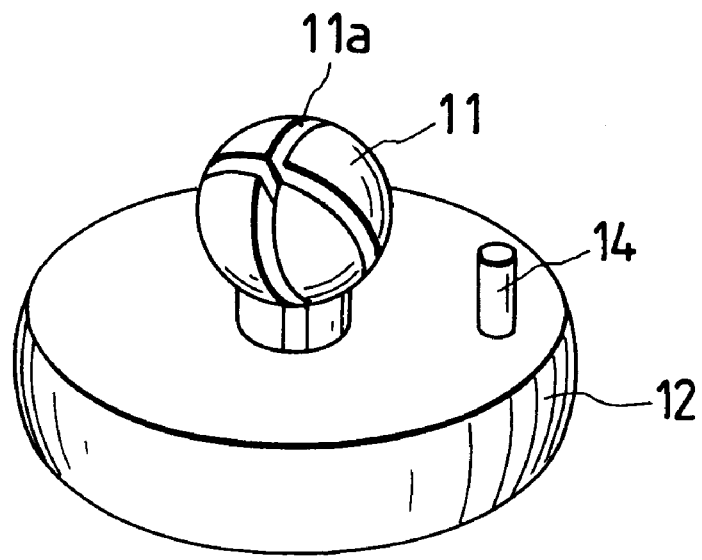
FIG. 3 is a perspective view showing the configuration of a spherical rotation shaft and a movable member of FIG. 1.
Figure 4:
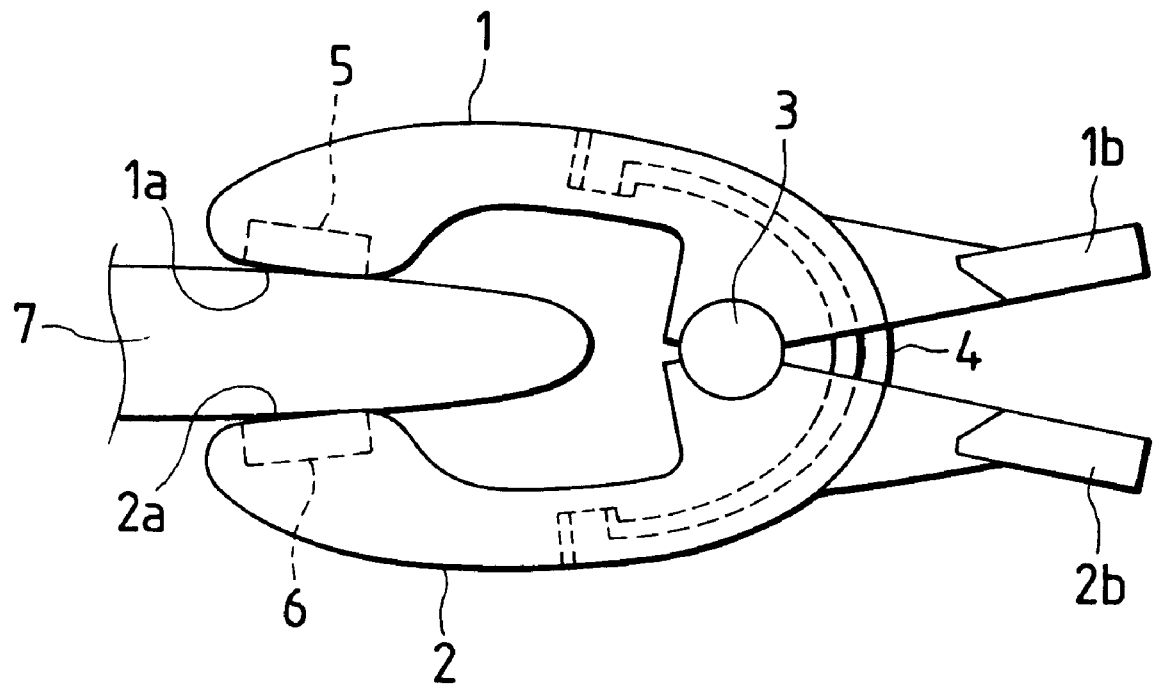
FIG. 4 is a aide view showing the configuration of an example of a pinch device for detecting a biomedical signal of the prior art.

FIGS. 1 to 3 show the configuration of the second embodiment of the pinch device for detecting a biomedical signal of the invention. In the figures, components which correspond to those of the prior art example shown in FIG. 4 are designated by the same reference numerals, and their description is omitted. The embodiment is characterized in that a disk-like movable member 12 is mounted to the vicinity of the tip end of one body member 1 via a spherical rotation shaft 11 so as to be rotatable in any direction, and a contact face 12a opposed to a contact face 2a which is formed at the tip end of another body member 2 is disposed on the movable member 12.

The spherical rotation shaft 11 is slidably fitted into a circular hole 1c which is formed in the vicinity of the tip end of the body member 1. Slits 11a passing through the center are formed in the shaft. The inner diameter of the circular hole 1c at an open side is squeezed. When the spherical rotation shaft 11 is compressed by a size corresponding to the width of the slits 11a, the rotation shaft can be attached to the hole through a diameter-reduced portion. An engagement plate 13 is fixed to the outside of the circular hole 1c so that the spherical rotation shaft 11 is inhibited by engagement from moving in the axial direction. A pin 14 erects on the upper face of the movable member 12. When the pin is engaged with A notch 1d formed in the inner face of the body member 1, the rotation of the spherical rotation shaft 11 is restricted to a predetermined range so that lead wires which will be described later are prevented from being broken. A spring member 4 is disposed on the outer peripheries of the body members 1 and 2 in the same manner as the prior art example shown in FIG. 4.

An LED 5 and a PD 6 are embedded into the contact face 12a of the movable member 12 and the contact face 12a of the body member 2, respectively. Lead wires 15 and 16 respectively connected to the LED 5 and the PD 6 elongate along grooves 17 and 18 formed in the inner faces of the body members 1 and 2 and are then drawn out to the outside through a lead wire drawing out hole 1e which is formed in the vicinity of the tip end of the body member 1.

According to the embodiment, even when both the faces of a measuring site such as an ear 7 are nonparallel with each other and inclined in an arbitrary direction as shown in FIG. 1, the movable member 12 is inclined with following the corresponding face. Therefore, the contact faces 12a and 2a can closely contact with the ear 7 and a biomedical signal such as a pulse wave can be correctly detected. Of course, the present invention is not limited by this embodiment. It is applicable for employing the feature such that the movable member supported on the body 12 by the axis to move it in a rotational direction along the body, in a rotational direction parallel to the body or the like.

In the embodiment described above, the LED 5 and the PD 6 are embedded into the contact face 12a of the movable member 12 and the contact face 2a of the body member 2, respectively. The arrangement relationship may be inverted. In place of the LED 5 or the PD 6, a plate-like electrode may be attached to the tip end of one of the body members. In place of the lead wires 15 and 16, a flexible circuit board on which predetermined wirings are formed may be used.

In the above, the embodiment in which the U-like spring is used has been described. Alternatively, the device may have a configuration in which a torsion coil spring is used.

As described above, according to the pinch device for detecting a biomedical signal of the invention, a movable member is mounted to the tip end of one of paired body members which are to pinch a measuring site of a living body, via a spherical rotation shaft so as to be rotatable in any direction, and the movable member has a contact face opposed to another contact face which is formed at a tip end of another one of the paired body members. Even when a measuring site is inclined in an arbitrary direction, therefore, the movable member is inclined with following a face of the measuring site. Consequently, the contact faces can closely contact with the measuring site, with the result that the pinch device can pinch the measuring site with a uniform pressure so that a biomedical signal can be correctly detected.

What is claimed is:

1. A pinch device for contacting a site of a living body, comprising:

a pair of body members which are opposed to each other, said body members being rotatably coupled to each other via a shaft portion;

a movable member mounted to a tip end of one of said paired body members through a spherical rotation shaft so as to be rotatable in any direction, and said movable member having a contact face opposed to another contact face which is formed at a tip end of another one of said paired body members; and a spring member urging said contact face of said movable member and said other contact face of said body member which is opposed to said movable member, in an approaching direction.

2. The pinch device of claim 1 further comprising:

a notch provided in said one of said body members connected to said moveable member; and a pin connected to a face of said moveable member, wherein the rotation of the spherical rotational shaft is restricted to a predetermined range when said pin is engaged with said notch.

3. The pinch device of claim 2 further comprising:

a wire connected to said moveable member, wherein said predetermined range of restriction of the spherical shaft prevents breakage of said wire.

4. A pinch device for detecting a biomedical signal which pinches a measuring site of a living body in order to detect a biomedical signal, comprising:

a pair of body members which are opposed to each other, said body members being rotatably coupled to each other via a shaft portion;

a movable member mounted to a tip end of one of said paired body members through a spherical rotation shaft so as to be rotatable in any direction, and said movable member having a contact face opposed to another contact face which is formed at a tip end of another one of said paired body members;

a spring member urging said contact face of said movable member and said other contact face of said body member which is opposed to said movable member, in an approaching direction;

a light emitting device connected to one of said contact faces for emitting light through a body portion; and a photo-detecting device connected to the other of said contact faces for detecting said transmitted light said body portion, wherein said detected transmitted light corresponds to the biomedical signal.

* * * * *